United States Patent [19]
Alpegiani et al.

[11] Patent Number: 5,777,104
[45] Date of Patent: Jul. 7, 1998

[54] CEPHEM DERIVATIVES AS ANTI-METASTATIC AGENTS

[75] Inventors: Marco Alpegiani, Milan; Pierluigi Bissolino, San Giorgio di Lomellina; Ettore Perrone, Boffalora Ticino; Enrico Pesenti, Cologno Monzese, all of Italy

[73] Assignee: Pharmacia & Upjohn S.p.A., Milan, Italy

[21] Appl. No.: 392,744

[22] PCT Filed: Jun. 24, 1994

[86] PCT No.: PCT/EP94/02059

§ 371 Date: Mar. 8, 1995

§ 102(e) Date: Mar. 8, 1995

[87] PCT Pub. No.: WO95/02603

PCT Pub. Date: Jan. 26, 1995

[30] Foreign Application Priority Data

Jul. 14, 1993 [GB] United Kingdom ............ 9314562

[51] Int. Cl.$^6$ ................................. A61K 31/545
[52] U.S. Cl. ............... 540/215; 540/225; 514/200; 514/18; 514/19
[58] Field of Search ................ 540/225, 215; 514/200, 18, 19

[56] References Cited

FOREIGN PATENT DOCUMENTS 0484870 5/1992 European Pat. Off.
2266525 3/1993 United Kingdom.

OTHER PUBLICATIONS

Bioorg Med Chem Lett 1, 21, 1991.

*Primary Examiner*—David Lukton
*Attorney, Agent, or Firm*—Oblon, Spivak, McClelland, Maier & Neustadt, P.C.

[57] ABSTRACT

The present invention relates to the use of known cephem derivatives of the formula:

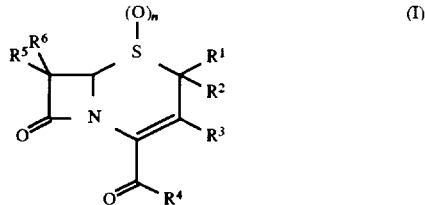

wherein n is zero, one or two; $R^1$ is hydrogen or an organic radical, $R^2$ represents halo or an organic radical or $R^1$ and $R^2$ taken together with the C-2 carbon atom of the cephem nucleus constitute a carbocyclic or heterocyclyl group; $R^3$ represents $R^2$ as defined above or an organic radical, $R^4$ is either $R^1$ or an organic group, $R^5$ is either $R^1$ as defined above or halo or $C_1$–$C_6$ alkoxy, $C_1$–$C_6$ alkylthio or $C_1$–$C_6$ acylamino;

$R^6$ is $R^2$ as defined above or an organic group, or a pharmaceutically acceptable salts thereof.

3 Claims, No Drawings

CEPHEM DERIVATIVES AS ANTI-METASTATIC AGENTS

The present invention relates to the use of cephem derivatives as anti-metastatic agents.

As known, malignancy of cancer is mainly due to metastasis. Because therapy usually fails to destroy multiple secondary tumor, their uncontrolled growth leads to death of patients. Only very few patients die from complications directly arising from primary tumor. Accordingly, there is a need in therapy of drugs able to prevent and/or block the metastatic spread.

Several cephem derivatives were described as having elastase inhibiting activity and can be used in the treatment of inflammatory and degenerative diseases caused by proteolytic enzymes in mammals including humans.

Now we have found that a selected class of compounds previously disclosed can prevent and/or block the metastatic spread of tumors in mammals, including humans.

Accordingly one object of the present invention is the use of a compound of formula (I)

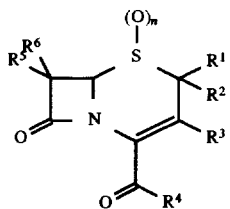

wherein n is zero, one or two;

$R^1$ is hydrogen or an optionally substituted $C_1-C_{12}$ alkyl, $C_2-C_{12}$ alkenyl, $C_2-C_{12}$ alkynyl, $C_6-C_{10}$ aryl, $C_3-C_8$ cycloalkyl, $C_5-C_8$ cycloalkenyl, or $C_7-C_{14}$ aralkyl, $C_8-C_{14}$ aralkenyl, $C_8-C_{14}$ aralkynyl, (cycloalkyl)alkyl, (cycloalkyl) alkenyl, heterocyclyl, (heterocyclyl)alkyl, (heterocyclyl) alkenyl;

$R^2$ represents an atom or group selected from the following:

(1) halogen (2) $R^1$ as defined above (3) an ether $OR^1$ wherein $R^1$ is as defined above (4) a thioether, sulphoxide or sulphone $—S(O)_nR^1$ wherein n and $R^1$ are as defined above (5) acyloxy $—OC(O)R^1$ wherein $R^1$ is as defined above;

(6) sulphonyloxy $—OS(O)_2R^1$ wherein $R^1$ is as defined above;

or $R^1$ and $R^2$ taken together form a methylene group of formula $=CHR^1$ or $=CH—CO_2R^1$ or $=CH—COR^1$ wherein $R^1$ is as defined above; or $R^1$ and $R^2$ taken together with the C-2 carbon atom of the cephem nucleus constitute a carbocyclic or heterocyclyl group;

$R^3$ represents one of the following:

(1) $R^2$ as defined above (2) an acyl group $—C(O)R^1$, $—C(O)OR^1$ or $—CO_2H$ wherein $R^1$ as defined above (3) on oxymethyl group $—CH_2—OR^1$ wherein $R^1$ is as defined above (4) a thiomethyl group or a derivative thereof of formula $—CH_2S(O)_nR^1$ wherein n and $R^1$ are as defined above (5) an acyloxymethyl group $—CH_2OC(O)R^1$ wherein $R^1$ is as defined above or a $—CH_2O—R^7$ wherein $R^7$ is a mono, di- or tripeptide composed of D or L α-aminoacids chosen from Ala, Gly, Val, Leu, Ile, Phe and with the terminal amino group either free or protected as an amide $—NHCOR^1$ or sulfonamide $—NHSO_2R^1$ wherein $R^1$ is as defined above (6) an acylthiomethyl group $—CH_2SC(O)R^1$ wherein $R^1$ is as defined above (7) a sulphonyloxymethyl group $—CH_2—OSO_2R^1$ wherein $R^1$ is as defined above (8) a group of formula $—CH_2-Z-NR^1R^8$ wherein Z is a bond, $—O$ $C(O)—$ or $—OS(O)_2—$, $R^1$ is as defined above and $R^8$, being the same or different, is as defined above for $R^1$; or $R^1$ and $R^8$ taken together with the nitrogen atom to which they are attached represent a heterocyclic ring;

(9) ammoniomethyl $—CH_2N^+R^1R^8R^9$ wherein $R^1$ and $R^8$ are as defined above and $R^9$, being the same or different, is as defined for $R^1$; or $R^1$ is alkyl and $R^8$ and $R^9$ together with the nitrogen atom to which they are attached represent a heterocyclic ring;

$R^4$ is either:

(1) a group $R^1$ wherein $R^1$ is as defined above (2) a group $OR^1$ wherein $R^1$ is as defined above (3) a group $SR^1$ wherein $R^1$ is as defined above (4) a group $NR^1R^5$ wherein $R^1$ and $R^8$ are as defined above;

$R^5$ is either $R^1$ as defined above or halogen or $C_1-C_6$ alkoxy, $C_1-C_6$ alkylthio or $C_1-C_6$ acylamino;

$R^6$ is a group selected from the following:

(1) $R^2$ as defined above (2) a group of formula $-Z-N(R^1)R^8$ wherein Z, $R^1$ and $R^8$ are as defined above (3) a group of formula $—NR^8C(O)R^1$ wherein $R^1$ and $R^8$ are as defined above, or $R^1$ and $R^8$ taken together with the aminocarbonyl group to which they are attached constitute a heterocyclic ring (4) an acylamino group $—NHR^7$ wherein $R^7$ is as defined above (5) an ammonio group $—N^+R^1R^8R^9$ wherein $R^1$, $R^8$ and $R^9$ are as defined above;

or $R^5$ and $R^6$ taken together with the C-7 carbon atom of the cephem nucleus constitute a carbocyclic or heterocyclic ring;

or $R^5$ and $R^6$ taken together constitute a methylene group of formula $=CHR^1$, $=CH—CO—R^1$ or $=CH—SO_2R^1$ wherein $R^1$ is as defined above or a pharmaceutically acceptable salt thereof, in the preparation of a medicament for use in preventing and/or treating the metastatic spread of tumors.

A further object the present invention is to provide a compound of formula (I), as defined above, or a pharmaceutically acceptable salt thereof, for use in preventing and/or treating the metastatic spread of tumors.

The $C_1-C_{12}$ alkyl group is a straight or branched alkyl group such as methyl, ethyl, n-propyl, isopropyl, n-butyl, isobutyl, sec-butyl, tert-butyl, n-pentyl, n-hexyl and so on.

The $C_2-C_{12}$ alkenyl group is a straight or branched alkenyl group such as vinyl, allyl, crotyl, 2-methyl-1-propenyl, 1-methyl-1-propenyl, butenyl, pentenyl and so on.

The $C_2-C_{12}$ alkynyl group is a straight or branched alkynyl group such as ethynyl, propargyl, 1-propynyl, 1-butynyl, 2-butynyl and so on.

The $C_6-C_{10}$ aryl group is a monocyclic or bicyclic aromatic hydrocarbon group of 6 to 10 carbon atoms, such as phenyl and naphtyl.

The $C_3-C_8$ cycloalkyl group is a saturated carbocyclic group of 3 to 6 carbon atoms, such as cyclopropyl, cyclobutyl, cyclopentyl, cyclohexyl and so on.

The $C_5$–$C_8$ cycloalkenyl group is an unsaturated carbocyclic group such as cyclopentenyl, cyclohexenyl and so on.

The $C_7$–$C_{14}$ aralkyl group is an alkyl group of 1 to 4 carbon atoms linked to a monocyclic or bicyclic aromatic hydrocarbon group of 6 to 10 carbon atoms. Examples of aralkyl groups are benzyl, phenylethyl and naphtylmethyl.

The $C_8$–$C_{14}$ aralkenyl group is an alkenyl group of 2 to 4 carbon atoms linked to a monocyclic or bicyclic aromatic hydrocarbon group of 6 to 10 carbon atoms. Examples of aralkenyl groups are styryl, 2-phenyl-1-propenyl, 3-phenyl-2-butenyl, 2-naphtylethenyl and so on.

The $C_8$–$C_{14}$ aralkynyl group is an alkynyl group of 2 to 4 carbon atoms linked to a monocyclic or bicyclic aromatic hydrocarbon group of 6 to 10 carbon atoms. Examples of aralkynyl groups are 2-phenylethynyl, 2-naphtylethynyl and so on.

The (cycloalkyl)alkyl group is an alkyl group of 1 to 4 carbon atoms linked to a cycloalkyl group.

The (cycloalkyl)alkenyl group is an alkenyl group of 2 to 4 carbon atoms linked to a cycloalkyl group or to an aryl group.

The heterocyclyl group is a 3- to 6-membered, saturated or unsaturated heterocyclyl ring, containing at least one heteroatom selected from O, S and N, which is optionally fused to a second 5- or 6-membered, saturated or unsaturated heterocyclyl group or to a cycloalkyl group or to an aryl group.

In particular, the heterocyclyl group may be for example a tetrazole, thiadiazole, pyrrole, triazole, imidazole, oxazole, thiophene, pyridine, pyrazine, triazine, morpholine and the like.

The (heterocyclyl)alkyl group is an alkyl group of 1 to 4 carbon atoms linked to a heterocyclyl group.

The (heterocyclyl)alkenyl group is an alkenyl group of 2 to 4 carbon atoms linked to a heterocyclic group.

The term halogen (or halo) preferably encompasses fluorine, chlorine or bromine.

The $C_1$–$C_6$ alkoxy group is a straight or branched alkoxy group such as methoxy, ethoxy, n-propoxy, isopropoxy, n-butoxy, isobutoxy, sec-butoxy, tert-butoxy, n-pentoxy, n-hexyloxy and so on.

The $C_1$–$C_6$ alkylthio group is a straight or branched alkylthio group such as methylthio, ethylthio, n-propylthio, isopropylthio, n-butylthio, isobutylthio, sec-butylthio, tert-butylthio, n-pentylthio, n-hexylthio and so on.

The $C_1$–$C_6$ acylamino group is a straight or branched acylamino group such as formamido, acetamido, propionamido, pivalamido and so on.

The above said alkyl, alkenyl, alkynyl, cycloalkyl, cycloalkenyl, aryl, aralkyl, aralkenyl, aralkynyl, (cycloalkyl)alkyl, (cycloalkyl)alkenyl, heterocyclyl, (heterocyclyl)alkyl, (heterocyclyl)alkenyl, alkoxy, alkylthio, acylamino groups can be either unsubstituted or substituted by one or more substituents selected from the following ones:

halo (i.e., fluoro, bromo, chloro or iodo);

hydroxy or oxo;

nitro;

azido;

mercapto (—SH);

amino (i.e., —NH$_2$, or —NHR' or —NR'R") wherein R' and R", which are the same or different, are $C_1$–$C_{12}$ straight or branched alkyl or phenyl or benzyl;

formyl (i.e., —CHO);

cyano;

carboxy(alkyl) (i.e., (CH$_2$)$_t$COOH or (CH$_2$)$_t$COOR') wherein R' is as defined above and t is 0, 1, 2 or 3;

sulpho (i.e., —SO$_3$H);

acyl (i.e., —C(O)R') wherein R' is as defined above or trifluoroacetyl (i.e., —C(O)CF$_3$);

carbamoyl (i.e., —CONH$_2$); N-methylcarbamoyl (i.e., —CONHCH$_3$) or N-carboxymethylcarbamoyl (i.e., —CONHCH$_2$COOH);

carbamoyloxy (i.e., —OCONH$_2$);

acyloxy (i.e., —OC(O)R') wherein R' is as defined above or formyloxy (i.e., —OC(O)H);

alkoxycarbonyl or benzyloxycarbonyl (i.e., —C(O)OR') wherein R' is as defined above;

alkoxycarbonyloxy or benzyloxycarbonyloxy (i.e., —OC(O)OR') wherein R' is as defined above;

alkoxy, phenoxy or benzyloxy (i.e., —OR') wherein R' is as defined above;

alkylthio, phenylthio or benzylthio (i.e., —SR') wherein R' is as defined above;

alkylsulphinyl, phenylsulphinyl or benzylsulphinyl (i.e., —S(O)R') wherein R' is as defined above;

alkylsulphonyl, phenylsulphonyl or benzylsulphonyl (i.e., —S(O)$_2$R') wherein R' is as defined above;

acylamino (i.e., —NHC(O)R''' or —NHC(O)OR''') wherein R''' is $C_1$–$C_{12}$ straight or branched alkyl, phenyl, benzyl, CH$_2$CH$_2$COOH or CH$_2$CH$_2$CH$_2$COOH;

sulphonamido (i.e., —NHSO$_2$R') wherein R' is as defined above;

guanidino (i.e., —NHC(=NH)NH$_2$);

$C_1$–$C_4$ alkyl, $C_2$–$C_4$ alkenyl or alkynyl;

$C_3$–$C_6$ cycloalkyl;

phenyl substituted methyl selected from chloromethyl, fluoromethyl, difluoromethyl, trifluoromethyl, aminomethyl, N,N-dimethylaminomethyl, azidomethyl, cyanomethyl, carboxymethyl, sulphomethyl, carbamoylmethyl, carbamoyloxymethyl, hydroxymethyl, $C_1$–$C_4$ alkoxycarbonylmethyl, guanidinomethyl.

The carboxyl-protecting group may, for example, be a lower alkyl group such as methyl, ethyl, propyl, isopropyl or tert-butyl; a halogenated lower alkyl group such as a 2,2,2-trichoroethyl or a 2,2,2-trifluoroethyl; a lower alkanoyloxyalkyl group such as acetoxymethyl, propionyloxymethyl, pivaloyloxymethyl, 1-acetoxyetyl, 1-propionyloxyethyl; a lower alkoxycarbonyloxyalkyl group such as 1-(methoxycarbonyloxy)ethyl, 1-ethoxycarbonyloxy)ethyl, 1-(isopropoxycarbonyloxy)ethyl; a lower alkenyl group such as 2-propenyl, 2-chloro-2-propenyl, 3-methoxycarbonyl-2-propenyl, 2-methyl-2-propenyl, 2-butenyl, cinnamyl; an aralkyl group such as benzyl, p-methoxybenzyl, 3,4-dimethoxybenzyl, o-nitrobenzyl, p-nitrobenzyl, benzhydryl, bis(p-methoxyphenyl)methyl; a (5-substituted 2-oxo-1,3-dioxol-4-yl)methyl group such as (5-methyl-2-oxo-1,3-dioxol-4-yl)methyl; a lower alkylsilyl group such as trimethylsilyl, tert-butyldimethylsilyl, tert-butyldiphenylsilyl, triphenylsilyl; or an indanyl group; a phtalidyl group; a pyranyl group; a methoxymethyl or methylthiomethyl group; a 2-methoxyethoxymethyl group. Particularly preferred are a tert-butyl group, a p-nitrobenzyl group, a p-methoxybenzyl group, a benzhydryl group, a tert-butyldimethylsilyl, tert-butyldiphenylsilyl group or a propenyl group.

The amino, hydroxy or mercapto protecting groups possibly present may be those usually employed in the chemistry of penicillins and cephalosporins for this kind of functions. They may be, for instance, optionally substituted, especially halo-substituted, acyl groups, e.g. acetyl, monochloroacetyl, dichloroacetyl, trifluoroacetyl, benzoyl or p-bromophenacyl; triarylmethylgroups, e.g. triphenylmethyl; silyl groups, in particular trimethylsilyl, dimethyl-tert-butylsilyl, diphenyl-tert-butylsilyl,; or also groups such as tert-butoxycarbonyl, p-nitrobenzyloxycarbonyl, 2,2,2-trichloroethoxycarbonyl, benzyl and pyranyl. Preferred protecting groups of the hydroxy function are p-nitrobenzyloxycarbonyl; allyloxycarbonyl; dimethyl-tert-butylsilyl; diphenyl-tert-butylsilyl; trimethylsilyl; 2,2,2-trichloroethoxycarbonyl; benzyl; dimethoxybenzyl; p-methoxybenzyloxycarbonyl; p-bromophenacyl; triphenylmethyl, pyranyl, methoxymethyl, benzhydryl, 2-methoxyethoxymethyl, formyl, acetyl, tricloroacetyl.

As already said, the invention includes within its scope the salts of those compounds of formula (I) that have salt-forming groups, especially the salts of the compounds having a carboxylic group, a basic group (e.g. an amino or guanidino group), or a quaternary ammonium group. The salts are especially physiologically tolerable salts, for example alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example hydrochloric acid, sulphuric acid, carboxylic and sulphonic organic acids (e.g. acetic, trifluoroacetic, p-toluensulphonic acid). Some compounds of formula (I) which contain a carboxylate and an ammonium group may exist as zwitterions; such salts are also part of the present invention.

The present invention encompasses all the possible stereoisomers as well as their racemic or optically active mixtures.

Furthermore, physiologically hydrolizable esters, hydrates and solvates of compounds of formula (I) are included within the scope of the present invention.

The physiologically hydrolizable esters of the compounds (I) may include, for example, methoxycarbonylmethyl, 1-methoxycarbonyloxy-1-ethyl, indanyl, phtalidyl, methoxymethyl, pivaloyloxymethyl, glycyloxymethyl, phenylglycyloxymethyl or 5-methyl-2-oxo-1,3-dioxolan-4-yl esters, and other physiologically hydrolizable esters which have been widely used in the technical fields of penicilin and cephalosporin antibiotics: more preferably, methoxycarbonyloxymethyl, 1-methoxycarbonyloxy-1-ethyl, methoxymethyl or pivaloyloxymethyl; and most preferably, methoxycarbonyloxymethyl or methoxymethyl.

Typical solvates of the cephalosporin compounds of formula (I) may include solvates with water miscible solvents, e.g. methanol, ethanol, acetone or acetonitrile or acetonitrile; and more preferably, ethanol.

Preferred compounds of formula (I), according to the invention, are the compounds of the formula (Ia)

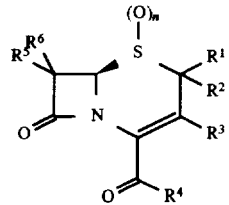

wherein n, $R^1$, $R^2$, $R^3$, $R^4$, $R^5$, and $R^6$, are as defined above, and the pharmaceutically acceptable salts thereof. Examples of compounds according to the present invention are the following:

1) (6R,7S)-2-(2,2-Dimethyl-propionyl)-4-(6-hydroxy-2-methyl-5-oxo-2,5-dihydro-|1,2,4|triazin-3-ylsulfanyl)-7-methoxy-3-methyl-5,5-dioxo-5-thia-1-aza-bicyclo|4.2.0|oct-2-en-8-one
2) 2-Benzoyl-7-methoxy-4-(5-methyl-|1,3,4|thiadiazol-2-ylsulfanyl)-3-(5-methyl- |1,3,4|thiadiazol-2-ylsulfanylmethyl)-5,5-dioxo-5-thia-1-aza-bicyclo|4.2.0|oct-2-en-8-one
3) 2-(2,2-Dimethyl-propionyl)-7-methoxy-4-(1-methyl-1H-tetrazol-5-ylsulfanyl)-3-(1-methyl-1H-tetrazol-5-ylsulfanylmethyl)-5,5-dioxo-5-thia-1-aza-bicyclo|4.2.0|oct-2-en-8-one
4) 2-Benzoyl-4-(6-hydroxy-2-methyl-5-oxo-2,5-dihydro-|1,2,4|triazin-3-ylsulfanyl)-7-methoxy-3-methyl-5,5-dioxo-5-thia-1-aza-bicyclo|4.2.0|oct-2-en-8-one
5) 2-Benzoyl-7-methoxy-3-methyl-4-(1-methyl-1H-tetrazol-5-ylsulfanyl)-5,5-dioxo-5-thia-1-aza-bicyclo|4.2.0|oct-2-en-8-one
6) 2-(2,2-Dimethyl-propionyl)-7-methoxy-3-methyl-4-(5-methyl-|1,3,4|thiadiazol-2-ylsulfanyl)-5,5-dioxo-5-thia-1-aza-bicyclo|4.2.0|oct-2-en-8-one
7) 2-(2,2-Dimethyl-propionyl)-7-methoxy-4-(5-methyl-|1,3,4|thiadiazol-2-ylsulfanyl)-3-(5-methyl-|1,3,4|thiadiazol-2-ylsulfanylmethyl)-5,5-dioxo-5-thia-1-aza-bicyclo|4.2.0|oct-2-en-8-one
8) 2-Benzoyl-7-methoxy-4-(1-methyl-1H-tetrazol-5-ylsulfanyl)-3-(1-methyl-1H-tetrazol-5-ylsulfanylmethyl)-5,5-dioxo-5-thia-1-aza-bicyclo|4.2.0|oct-2-en-8-one
9) 7-Allyl-2-benzoyl-4-(5-methyl-|1,3,4|thiadiazol-2-ylsulfanyl)-3-(5-methyl-|1,3,4|thiadiazol-2-ylsulfanylmethyl)-5,5-dioxo-5-thia-1-aza-bicyclo|4.2.0|oct-2-en-8-one
10) 7-Allyl-2-(2,2-dimethyl-propionyl)-4-(5-methyl-|1,3,4|thiadiazol-2-ylsulfanyl)-3-(5-methyl-|1,3,4|thiadiazol-2-ylsulfanylmethyl)-5,5-dioxo-5-thia-1-aza-bicyclo|4.2.0|oct-2-en-8-one
11) 3-(6-Hydroxy-2-methyl-5-oxo-2,5-dihydro-|1,2,4|triazin-3-ylsulfanylmethyl)-7-methoxy-5,5-dioxo-2-(pyrrolidine-1-carbonyl)-5-thia-1-aza-bicyclo|4.2.0|oct-2-en-8-one
12) 1-(3-Acetoxymethyl-7-methoxy-5,5,8-trioxo-5-thia-1-aza-bicyclo|4.2.0|oct-2-enane-2-carbonyl)pyrrolidine-2-carboxilic acid
13) 1-|3-Acetoxymethyl-5,5,8-trioxo-7-(2,2,2-trifluoroacetylamino)-5-thia-1-aza-bicyclo|4.2.0|oct-2-enane-2-carbonyl|-pyrrolidine-2-carboxilic acid
14) 1-(7-Benzoylamino-3-methyl-5,5,8-trioxo-5-thia-1-aza-bicyclo|4.2.0|oct-2-enane-2-carbonyl)-pyrrolidine-2-carboxylic acid
15) 3-Methyl-5,5,8-trioxo-5-thia-1-aza-bicyclo|4.2.0|oct-2-ene-2-carboxylic acid 4-carboxy-benzyl ester
16) 2-Benzoyl-7-ethylsulfanyl-4-(5-methyl-|1,3,4|thiadiazol-2-ylsulfanyl)-3-(5-methyl-|1,3,4|thiadiazol-2-ylsulfanylmethyl)-5,5-dioxo-5-thia-1-aza-bicyclo|4.2.0|oct-2-en-8-one
17) 2-Benzoyl-7-ethylsulfanyl-3-methyl-4-(5-methyl-|1,3,4|thiadiazol-2-ylsulfanyl)-5,5-dioxo-5-thia-1-aza-bicyclo|4.2.0|oct-2-en-8-one
18) 3-(1-Methyl-1H-tetrazol-5-ylsulfanylmethyl)-5,5,8-trioxo-7-(2,2,2-trifluoro-acetylamino)-5-thia-1-aza-bicyclo|4.2.0|oct-2-ene-2-carboxylic acid 4-carboxy-benzyl ester
19) 2-Acetylamino-3-|7-methoxy-3-(1-methyl-1H-tetrazol-5-ylsulfanylmethyl)-5,5,8-trioxo-5-thia-1-aza-bicyclo|4.2.0|oct-2-enane-2-carbonylsulfanyl|-propionic acid
20) 2-Acetylamino-3-|7-allyl-3-(1-methyl-1H-tetrazol-5-ylsulfanylmethyl)-5,5,8-trioxo-5-thia-1-aza-bicyclo|4.2.0|oct-2-enane-2-carbonylsulfanyl|-propionic acid and the pharmaceutically acceptable salts thereof.

Cephems of formula (I) defined under the present invention are known compounds or can be prepared from known compounds by known methodologies.

For example, suitable methods for the preparation of the claimed compounds can be found in the following bibliografic references, listed according to the site of functionalization of the cephem nucleus:

2-substituted cephems: Noveau Journal de Chimie 1, 85 (1977); Synthetic Communations 15, 681 (1985); Chem. Pharm. Bull. 31 1482 (1983); Bull. Chem. Soc. Jpn. 56, 2185 (1983); Tetrahedon Letters 21, 1293, (1980); J. Org. Chem. 44, 811 (1979); Tetrahedron Letters 4751 (1978); J. Am. Chem. Soc. 100, 1886 (1978); J. Chem. Soc. Perkin I 2298 (1977); Tetrahedron Letters 3611 (1977); J. Chem. Soc. Chem. Comm. 671 (1973); Tetrahedron Letters 3717 (1972); U.S. Pat. No. 3,660,395; Eur. J. Med. Chem. 24, 599 (1989); J. Med. Chem. 14, 420 (1971); J. Med. Chem. 14, 426 (1971); Heterocycles 29, 1107 (1989); J. Med. Chem. 27, 1225 (1984).

3-substituted cephems: Heterocycles 24, 1653 (1986); J. Chem. Soc. Perkin I 1361 (1991); SynLett 389 (1990); SynLett 391 (1990); J. Org. Chem. 55, 5833 (1990); Tetrahedron Letters 31, 3389 (1983); Tetrahedron 41, 2025 (1985); Chem. Pharm. Bull. 33, 5534 (1985); J. Chem. Soc. Perkin I 2281 (1983); J. Org. Chem. 53, 983 (1988); Gazz. Chim. II. 115, 169 (1985); Tetrahedron 39, 461 (1983); J: Antibiotics 39, 380 (1986); J. Am. Chem. Soc. 108, 1685 (1986); J. Chem. Soc. Chem. Comm. 1012 (1974); Chem. Pharm. Bull. 28, 2116 (1980); Gazz. Chim. IC 110, 519 (1980); Phil. Trans. R. Soc. Lond. B 289, 173 (1980); Chem. Pharm. Bull. 28, 62 (1980); J. Antibiotics 37, 1441 (1984); Tetrahedon Letters 29, 6043 (1988); Tetrahedron Letters 29, 5739 (1988); Heterocycles 1799 (1986); J. Org. Chem. 54, 5828 (1989); J. Antibiotics 42, 159 (1989); Heterocycles 28, 657 (1989); SynLett 888 (1991); J. Antibiotics 43, 533 (1990), Eur. J. Med. Chem. 27, 875 (1992).

4-substituted cephems: Tetrahedron Letters 52, 5219 (1978); Tetrahedron Letters 33, 2915 (1977); J. Org. Chem. 51, 4723 (1986); Synthesis 52 (1986); J. Org. Chem. 35, 2429 (1970); J. Org. Chem. 35, 2430 (1970); U.S. Pat. No. 4,992,541-A; EP 0124001-A2; EP 0267723-A2; U.S. Pat. No. 4,547,371; J. Med. Chem. 33, 2522 (1990); Tetrahedron Letters 32, 6207 (1991); Eur. J. Med. Chem. 27, 875 (1992), J. Med. Chem. 20, 173 (1977); J. Med. Chem. 15, 1172 (1972); U.S. Pat. No. 5,077,286; PCT WO 89/10926.

7-substituted cephem: J. Org. Chem. 43, 3788 (1978); J. Org. Chem. 42, 2960 (1977); J. Org. Chem. 42, 3972 (1977); Tetrahedron Letters 1303 (1976); J. Med. Chem. 25, 457 (1982); Tetrahedron Letters 16, 1441 (1979); J. Chem Soc. Chem. Comm. 276 (1988); J. Chem. Soc. Perkin I 635 (1987); J. Org. Chem. 54, 3907 (1989); J. Antibiotics 52, 159 (1989); Tetrahedron Letters 30, 2375 (1989); Tetrahedron Letters 30, 2379 (1989) Thetrahedron Letters 375 (1972); Tetrahedron Letters 19, 1637 (1979).

As stated above, the compounds of the invention have been found to be active as anti-metastatic agents. Accordingly, they can be used in mammals, including humans, for preventing and/or treating the metastatic spread of tumors.

The antimetastatic activity of the compounds was proved experimentally in vivo against the highly metastatic B16F10 murine melanoma. B16F10 tumor cells were maintained in vitro by serial soil. For experimental purpose, tumor cells were pretreated in vitro with 1000γ for 6 hrs, whereas control were incubated with medium. Cells were then harvested and injected intravenously into C57/B16 mice at the concentration of $10^5$ cells/mouse. Animals were treated intraperitoneally with the compound for 6 days at the dose of 200 mg/kg. After 22 days mice were sacrificed and the number of lung metastatic foci were counted.

Data reported in table 1 show that a representative compound of the invention, namely (6R,7S)-2-(2,2-dimethylpropionyl)-4-(6-hydroxy-2-methyl-5-oxo-2,5-dihydro-|1,2, 4|triazin-3-ylsulfanyl)-7-methoxy-3-methyl-5,5-dioxo-5-thia-1-aza-bicyclo|4.2.0|oct-2-en-8-one (internal code FCE26238) is clearly active as antimetastatic agent. An evident reduction of the metastasis number was observed after in vitro pretreatment and after in vivo treatment. No evidence of toxicity was observed.

TABLE 1

| Group | Treatment with FCE26238 | | median number of metastasis |
|---|---|---|---|
| | in vitro | in vivo | (range) |
| Control | — | — | 20 (7–72) |
| | — | 200 mg/kg x6 | 4 (2–24) |
| | 1000γ x 6 hrs | — | 0 (0–0) |
| | 1000γ x 6 hrs | 200 mg/kg x6 | 0 (0–0) |

The compounds of the invention can be administered by the usual routes, for example, parenterally, e.g. by intravenous injection or infusion, intramuscularly, subcutaneously, topically or orally, intravenous injection or infusion being the preferred. The dosage depends on the age, weight and condition of the patient and on the administration route.

A suitable dosage for the compounds of the invention, e.g. FCE26238 for administration to adult humans may range from about 0.5 to about 300 mg per dose 1–4 times a day.

The pharmaceutical compositions of the invention may contain a compound of formula (I) or a pharmaceutically acceptable salt thereof, as the active substance, in association with one or more pharmaceutically acceptable excipients and/or carriers.

The pharmaceutical compositions of the invention are usually prepared following conventional methods and are administered in a pharmaceutically suitable form. For instance, solutions for intravenous injection or infusion may contain as carrier, for example, sterile water or, preferably, they may be in the form of sterile aqueous isotonic saline solutions.

Suspensions or solutios for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

In the form for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g. lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

An object of the invention is also to provide a method of treatment of the above mentioned pathological conditions comprising both separate and substantially contemporaneous administration of a composition containing a compound of formula (I), or a pharmaceutically acceptable salt thereof, and a pharmaceutical composition containing a different pharmaceutically active agent, typically an antitumor agent.

Antitumor agents that can be formulated with a compound of the invention or, alternatively, can be administered in a combined method of treatment are e.g. doxorubicin, daunomycin, epirubicin, idarubicin, etoposide, fluorouracil, paclitaxel, melphalan, cyclophosphamide, bleomycin, vinblastin and mitomycin or a mixture of two or more thereof.

The compounds of the invention can therefore be used in a treatment to ameliorate a cancer.

EXAMPLE A

Tablets:

| Ingredients | Per Tablet | Per 10,000 Tablets |
| --- | --- | --- |
| 1. Active ingredient Cpd of Form I | 40.0 mg | 400 g |
| 2. Corn Starch | 20.0 mg | 200 g |
| 3. Alginic acid | 20.0 mg | 200 g |
| 4. Sodium alginate | 20.0 mg | 200 g |
| 5. Magnesium Stearate | 1.3 mg | 13 g |
| | 101.3 mg | 1013 g |

Procedure for tablets:

Step 1. Blend ingredients No. 1, No. 2, No. 3 and No. 4 in a suitable mixer/blender.
Step 2. Add sufficient water portionwise to the blend from Step 1 with careful mixing after each addition. Such additions of water and mixing until the mass is of a consistency to permit its conversion to wet granules.
Step 3. The wet mass is converted to granules by passing it through an oscillating granulator using a number 8 mesh (2.38) screen.
Step 4. The wet granules are dried in an oven at 60° C. until dried.
Step 5. The dried granules are lubricated with ingredient no. 5.
Step 6. The lubricated granules are compressed on a suitable tablet press.

EXAMPLE B

Intramuscular injection:

| Ingredients | Per ml | Per liter |
| --- | --- | --- |
| 1. Active ingredient Cpd of Form I | 10.0 mg | 10 g |
| 2. Isotonic buffer solution pH 4.0. | q.s. | q.s. |

Procedure:

Step 1. Dissolve the active ingredient in the buffer solution.
Step 2. Aseptically filter the solution from step 1.

Step 3. The sterile solution is aseptically filled into sterile ampoules
Step 4. The ampoules are sealed under aseptic conditions.

We claim:

1. A method of inhibiting the metastatic spread of tumors comprising administering to a patient in need thereof an effective amount of a compound of formula (I)

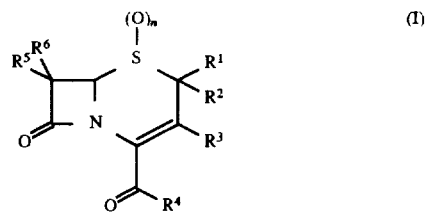

wherein n is zero, one or two;
$R^1$ is hydrogen or a $C_1$–$C_{12}$ alkyl, $C_2$–$C_{12}$ alkenyl, $C_2$–$C_{12}$ alkynyl, $C_6$–$C_{10}$ aryl, $C_3$–$C_8$ cycloalkyl, $C_5$–$C_8$ cycloalkenyl, $C_7$–$C_{14}$ aralkyl, $C_8$–$C_{14}$ aralkenyl, $C_8$–$C_{14}$ aralkynyl, (cycloalkyl)alkyl, (cycloalkyl)alkenyl, heterocyclyl, (heterocyclyl)alkyl, (heterocyclyl)alkenyl, each of which may be substituted by one or more substituents selected from:
halo;
hydroxy or oxo;
nitro;
azido;
mercapto;
amino, selected from —NH$_2$, —NHR' or —NR'R", wherein R' and R", which are the same or different, are $C_1$–$C_{12}$ straight or branched alkyl, phenyl or benzyl;
formyl;
cyano;
carboxy(alkyl), selected from (CH$_2$)$_t$COOH or (CH$_2$)$_t$COOR', wherein R' is as defined above and t is 0, 1, 2, or 3;
sulpho;
acyl selected from —C(O)R', wherein R' is as defined above or trifluoroacetyl;
carbamoyl, N-methylcarbamoyl or N-carboxymethylcarbamoyl;
carbamoyloxy;
acyloxy of the formula —OC(O)R', wherein R' is as defined above, or formyloxy;
alkoxycarbonyl or benzyloxycarbonyl of the formula —C(O)OR', wherein R' is as defined above;
alkoxycarbonyloxy or benzyloxycarbonyloxy of the formula —OC(O)OR', wherein R' is as defined above;
alkoxy, phenoxy or benzyloxy of the formula —OR', wherein R' is as defined above;
alkylthio, phenylthio or benzylthio of the formula —SR', wherein R' is as defined above;
alkylsulphinyl, phenylsulphinyl or benzylsulphinyl of the formula —S(O)R', wherein R' is as defined above;
alkylsulphonyl, phenylsulphonyl or benzylsulphonyl of the formula —S(O)$_2$R', wherein R' is as defined above;
acylamino of the formula —NHC(O)R'" or —NHC(O)OR'", wherein R'" is $C_1$–$C_{12}$ straight or branched alkyl, phenyl, benzyl, CH$_2$CH$_2$COOH or CH$_2$CH$_2$CH$_2$COOH;
sulphonamido of the formula —NHSO$_2$R', wherein R' is as defined above;

guanidino;
$C_1$–$C_4$ alkyl, $C_2$–$C_4$ alkenyl or alkynyl;
$C_3$–$C_6$ cycloalkyl;
phenyl
substituted methyl selected from the group consisting of chloromethyl, fluoromethyl, difluoromethyl, trifluoromethyl, aminomethyl, N,N-dimethylaminomethyl, azidomethyl, cyanomethyl, carboxymethyl, sulphomethyl, carbamoylmethyl, carbamoyloxymethyl, hydroxymethyl, $C_1$–$C_4$ alkoxycarbonylmethyl, and guanidinomethyl;

$R^2$ represents an atom or group selected from the following:
(1) halogen
(2) $R^1$ as defined above
(3) an ether $OR^1$ wherein $R^1$ is as defined above
(4) a thioether, sulphoxide or sulphone —$S(O)_n R^1$ wherein n and $R^1$ are as defined above
(5) acyloxy —$OC(O)R^1$ wherein $R^1$ is as defined above;
(6) sulphonyloxy —$OS(O)_2 R^1$ wherein $R^1$ is as defined above; or $R^1$ and $R^2$ taken together form a methylene group of formula =$CHR^1$ or =$CH$—$CO_2R^1$ or =$CH$—$COR^1$ wherein $R^1$ is as defined above; or $R^1$ and $R^2$ taken together with the C-2 carbon atom of the cephem nucleus constitute a carbocyclic or heterocyclyl group;

$R^3$ represents one of the following:
(1) $R^2$ as defined above
(2) an acyl group —$C(O)R^1$, —$C(O)OR^1$ or —$CO_2H$ wherein $R^1$ as defined above
(3) an oxymethyl group —$CH_2$—$OR^1$ wherein $R^1$ is as defined above
(4) a thiomethyl group or a derivative thereof of formula —$CH_2S(O)_n R^1$ wherein n and $R^1$ are as defined above
(5) an acyloxymethyl group —$CH_2OC(O)R^1$ wherein $R^1$ is as defined above or a —$CH_2O$—$R^7$ wherein $R^7$ is a mono, di- or tripeptide composed of D or L α-aminoacids chosen from Ala, Gly, Val, Leu, Ile, Phe and with the terminal amino group either free or protected as an amide —$NHCOR^1$ or sulfonamide —$NHSO_2R^1$ wherein $R^1$ is as defined above
(6) an acylthiomethyl group —$CH_2SC(O)R^1$ wherein $R^1$ is as defined above
(7) a sulphonyloxymethyl group —$CH_2$—$OSO_2R^1$ wherein $R^1$ is as defined above
(8) a group of formula —$CH_2$-Z-$NR^1R^8$ wherein Z is a bond, —O C(O)— or —$OS(O)_2$—, $R^1$ is as defined above and $R^8$, being the same or different, is as defined above for $R^1$; or $R^1$ and $R^8$ taken together with the nitrogen atom to which they are attached represent a heterocyclic ring;
(9) ammoniomethyl —$CH_2N^+R^1R^8R^9$ wherein $R^1$ and $R^8$ are as defined above and $R^9$, being the same or different, is as defined for $R^1$; or $R^1$ is alkyl and $R^8$ and $R^9$ together with the nitrogen atom to which they are attached represent a heterocyclic ring;

$R^4$ is either:
(1) a group $R^1$ wherein $R^1$ is as defined above
(2) a group $OR^1$ wherein $R^1$ is as defined above
(3) a group $SR^1$ wherein $R^1$ is as defined above
(4) a group $NR^1R^5$ wherein $R^1$ and $R^8$ are as defined above;

$R^5$ is either $R^1$ as defined above or halogen or $C_1$–$C_6$ alkoxy, $C_1$–$C_6$ alkylthio or $C_1$–$C_6$ acylamino;

$R^6$ is a group selected from the following:

(1) $R^2$ as defined above
(2) a group of formula -Z-$N(R^1)R^8$ wherein Z, $R^1$ and $R^8$ are as defined above
(3) a group of formula —$NR^8C(O)R^1$ wherein $R^1$ and $R^8$ are as defined above, or $R^1$ and $R^8$ taken together with the aminocarbonyl group to which they are attached constitute a heterocyclic ring
(4) an acylamino group —$NHR^7$ wherein $R^7$ is as defined above
(5) an ammonio group —$N^+R^1R^8R^9$ wherein $R^1$, $R^8$ and $R^9$ are as defined above;

or $R^1$ and $R^6$ taken together with the C-7 carbon atom of the cephem nucleus constitute a carbocyclic or heterocyclic ring;

or $R^5$ and $R^6$ taken together constitute a methylene group of formula =$CHR^1$, =$CH$—$CO$—$R^1$ or =$CH$—$SO_2R^1$, wherein $R^1$ is as defined above;

with the proviso that when $R^3$ is a group of the formula $CH_2S(O)_n R'$, wherein n is zero and $R'$ is a $C_1$–$C_{12}$ alkyl substituted with an amino substituent, said amino substituent has the formula —$NH_2$, —$NHR'$ or $NR'R''$, wherein $R'$ and $R''$, which may be the same or different, are $C_1$–$C_{12}$ straight or branched alkyl, phenyl or benzyl; or a pharmaceutically acceptable salt thereof.

2. The method of claim 1, wherein said compound is selected from the group consisting of:

(a) (6R, 7S)-2-(2,2-dimethyl-propionyl)-4-(6-hydroxy-2-methyl-5-oxo-2,5-dihydro-|1,2,4|triazin-3-ylsulfanyl)-7-methoxy-3-methyl-5,5-dioxo-5-thia-1-aza-bicyclo |4.2.0|oct-2-en-8-one;

(b) 2-benzoyl-7-methoxy-4-(5-methyl-|1,3,4|thiadiazol-2-ylsulfanyl)-3-(5-methyl-|1,3,4|thiadiazol-2-ylsulfanylmethyl)-5,5-dioxo-5-thia-1-aza-bicyclo |4.2.0|oct-2-en-8-one;

(c) 2-(2,2-dimethyl-propionyl)-7-methoxy-4-(1-methyl-1H-tetrazol-5-ylsulfanyl)-3-(1-methyl-1H-tetrazol-5-ylsulfanylmethyl)-5,5-dioxo-5-thia-1-aza-bicyclo |4.2.0|oct-2-en-8-one;

(d) 2-benzoyl-4-(6-hydroxy-2-methyl-5-oxo-2,5-dihydro-|1,2,4|triazin-3-ylsulfanyl)-7-methoxy-3-methyl-5,5-dioxo-5-thia-1-aza-bicyclo|4.2.0|oct-2-en-8-one;

(e) 2-benzoyl-7-methoxy-3-methyl-4-(1-methyl-1H-tetrazol-5-ylsulfanyl)-5,5-dioxo-5-thia-1-aza-bicyclo |4.2.0|oct-2-en-8-one;

(f) 2-(2,2-dimethyl-propionyl)-7-methoxy-3-methyl-4-(5-methyl-|1,3,4|thiadiazol-2-ylsulfanyl)-5,5-dioxo-5-thia-1-aza-bicyclo|4.2.0|oct-2-en-8-one;

(g) 2-(2,2-dimethyl-propionyl)-7-methoxy-4-(5-methyl-|1,3,4|thiadiazol-2-ylsulfanyl-3-(5-methyl-|1,3,4| thiadiazol-2-ylsulfanylmethyl)-5,5-dioxo-5-thia-1-aza-bicyclo|4.2.0|oct-2-en-8-one;

(h) 2-benzoyl-7-methoxy-4-(1-methyl-1H-tetrazol-5-ylsulfanyl)-3-(1-methyl-1H-tetrazol-5-ylsulfanylmethyl)-5,5-dioxo-5-thia-1-aza-bicyclo |4.2.0|oct-2-en-8-one;

(i) 7-allyl-2-benzoyl-4-(5-methyl-|1,3,4|thiadiazol-2-ylsulfanyl)-3-(5-methyl-|1,3,4|thiadiazol-2-ylsulfanylmethyl)-5,5-dioxo-5-thia-1-azabicyclo |4.2.0|oct-2-en-8-one;

(j) 7-allyl-2-(2,2-dimethyl-propionyl)-4-(5-methyl|1,3,4| thiadiazol-2-ylsulfanyl)-3-(5-methyl|1,3,4|thiadiazol-2-ylsulfanylmethyl)-5,5-dioxo-5-thia-1-aza-bicyclo |4.2.0|oct-2-en-8-one;

(k) 3-(6-hydroxy-2-methyl-5-oxo-2,5-dihydro|1,2,4| triazin-3-ylsulfanylmethyl)-7-methoxy-5,5-dioxo-2-

(pyrrolidine-1-carbonyl)-5-thia-1-azabicyclo[4.2.0]
oct-2-en-8-one;

(l) 1-(3-acetoxymethyl-7-methoxy-5,5,8-trioxo-5-thia-1-aza-bicyclo[4.2.0]oct-2-enane-2-carbonyl)pyrrolidine-2-carboxylic acid;

(m) 1-[3-acetoxymethyl-5,5,8-trioxo-7-(2,2,2-trifluoroacetylamino)-5-thia-1-aza-bicyclo[4.2.0]oct-2-enane-2-carbonyl]-pyrrolidine-2-carboxylic acid;

(n) 1-(7-benzoylamino-3-methyl-5,5,8-trioxo-5-thia-1-aza-bicyclo[4.2.0]oct-2-enane-2-carbonyl)-pyrrolidine-2-carboxylic acid;

(o) 3-methyl-5,5,8-trioxo-5-thia-1-azabicyclo[4.2.0]oct-2-ene-2-carboxylic acid 4-carboxy-benzyl ester;

(p) 2-benzoyl-7-ethylsulfanyl-4-(5-methyl[1,3,4]thiadiazol-2-ylsulfanyl)-3-(5-methyl-[1,3,4]thiadiazol-2-ylsulfanylmethyl)-5,5-dioxo-5-thia-1-aza-bicyclo[4.2.0]oct-2-en-8-one;

(q) 2-benzoyl-7-ethylsulfanyl-3-methyl-4-(5-methyl[1,3,4]thiadiazol-2-ylsulfanyl)-5,5-dioxo-5-thia-1-azabicyclo[4.2.0]oct-2-en-8-one;

(r) 3-(1-methyl-1H-tetrazol-5-ylsulfanylmethyl)-5,5,8-trioxo-7-(2,2,2-trifluoro-acetylamino)-5-thia-1-aza-bicyclo[4.2.0]oct-2-ene-2-carboxylic acid 4-carboxybenzyl ester;

(s) 2-acetylamino-3-[7-methoxy-3-(1-methyl-1H-tetrazol-5-ylsulfanylmethyl)-5,5,8-trioxo-5-thia-1-aza-bicyclo[4.2.0]oct-2-enane-2-carbonylsulfanyl]-propionic acid];

(t) 2-acetylamino-3-[7-allyl-3-(1-methyl-1H-tetrazol-5-ylsulfanylmethyl)-5,5,8-trioxo-5-thia-1-aza-bicyclo[4.2.0]oct-2-enane-2-carbonylsulfanyl]-propionic acid;

or a pharmaceutically acceptable salt thereof.

3. The method of inhibiting the metastatic spread of tumors of claim 1, wherein said compound of formula (I) is:

(6R,7S)-2-(2,2-dimethyl-propionyl)-4-(6-hydroxy-2-methyl-5-oxo-2,5-dihydro-[1,2,4]triazin-3-ylsulfanyl)-7-methoxy-3-methyl-5,5-dioxo-5-thia-1-aza-bicyclo[4.2.0]-oct-2-en-8-one.

* * * * *